United States Patent [19]

Dal Moro et al.

[11] 4,323,556

[45] Apr. 6, 1982

[54] SOLID FORMULATIONS CONTAINING PHEROMONES AND METHOD OF USING SAME

[75] Inventors: Anacleto Dal Moro; Franco Pinamonti; Amedeo Capizzi, all of Milan, Italy

[73] Assignee: Montedison S.p.A., Milan, Italy

[21] Appl. No.: 267,059

[22] Filed: May 26, 1981

Related U.S. Application Data

[63] Continuation-in-part of Ser. No. 210,727, Nov. 26, 1980, abandoned.

[30] Foreign Application Priority Data

Jan. 23, 1980 [IT]  Italy ................................ 19390 A/80

[51] Int. Cl.$^3$ ............................................ A01N 17/14
[52] U.S. Cl. ..................................................... 424/84
[58] Field of Search ......................................... 424/84

[56] References Cited

U.S. PATENT DOCUMENTS

| | | | |
|---|---|---|---|
| 2,123,929 | 7/1938 | Bovsquet | 424/174 |
| 2,800,457 | 7/1957 | Green et al. | 252/316 |
| 2,800,458 | 7/1957 | Green | 252/316 |
| 3,097,128 | 7/1963 | Sprinkle et al. | 424/84 |
| 3,577,515 | 5/1971 | Vandegaer | 424/32 |
| 3,791,983 | 2/1974 | Maierson | 424/84 |
| 3,954,968 | 5/1976 | McKibben | 424/84 |
| 3,961,051 | 6/1976 | Emodi | 424/174 |
| 3,962,428 | 6/1976 | Emodi | 424/174 |
| 4,017,030 | 4/1977 | Coplan et al. | 239/44 |
| 4,160,335 | 7/1979 | Von Kohorn et al. | 424/84 |
| 4,171,355 | 10/1979 | Stubbs et al. | 424/174 |
| 4,219,542 | 8/1980 | Klun et al. | 424/84 |

OTHER PUBLICATIONS

"Controlled Release of Pheromones Through Multi-Layered Polymeric Dispensers", Agis F. Kydonieus and Inja K. Smith–Hercon Div., Health–Chem. Corp., New York and Morton Beroza, M. Beroza & Assoc., Silver Spring, Md, pp. 283-294.

*Primary Examiner*—Donald B. Moyer

[57] ABSTRACT

There are disclosed solid formulations having, as an active substance, a sex pheromone, more particularly a sex pheromone of insect, supported by an inert carrier coated with a film-generating resin, and as components: a wetting agent, a dispersant, a sticker, an ultraviolet stabilizer and an antioxidant. Said formulations are used to control insects by hindering mating of the insects (mating disruption).

16 Claims, No Drawings

SOLID FORMULATIONS CONTAINING PHEROMONES AND METHOD OF USING SAME

This application is a continuation-in-part of Ser. No. 210,727, filed Nov. 26, 1980, now abandoned.

BACKGROUND OF THE INVENTION

In recent years, pheromones have acquired great importance in the research for methods for the control of insects noxious to agricultural cultivations.

The pheromones are secreted on the outer surface of the insect body and, depending on the type of reaction that they induce, may be subdivided into: aggregating, tracing or marking, sexual, or alarming pheromones, or they may be of other types.

The diffused and interesting pheromones, due to the application possibilities in the control of insects, are the sex pheromones which are secreted more frequently by the females, but also by the males, and which attract the individuals of the opposite sex for the mating. The use of the pheromones for the control of the insects is actually based on the principle that small quantities of such compounds, obtained by synthesis, will cause the same reactions as those induced by the male or female insect which secrete the natural attractants (pheromones).

Practically, the synthetised sex pheromones are applied both for monitoring the growth of the populations of the noxious species, as well as for controlling the harmful species by hindering the matings (mating disruption).

In the latter case, the sex pheromones have the task of either partially or completely substituting the insecticides and of directly controlling the insects by modifying their behavior.

The techniques used for achieving this purpose are two: mass trapping and confusion. The first, (mass trapping), has for its aim the attraction to, and catching in, small trapping cages of the greatest possible number of insects. The second, (confusion method), consists in diffusing the pheromones in the air so as to incapacitate the males or females to "feel" and "locate" the individuals of the opposite sex, thus hindering the mating.

In practice, the attractant may be diffused by distributing the product at various points in suitably distanced zones, or by nebulizing the product uniformly over the whole cultivation.

In the first instance, use is made of evaporators in which the pheromones are englobated or incorporated into substances of different nature, suited for causing the volatilization at a suitable rate and persistance. However, such systems are rather expensive due to the high cost of the evaporators and of labor.

A less expensive and elaborate system consists in distributing the pheromone over the whole zone by nebulizing it both from the ground and from aircraft, and by having recourse to special formulations with controlled release.

A number of known slow-release formulation systems may consist of aqueous suspensions of pheromone-containing microcapsules having walls made of polyamides (U.S. Pat. No. 3,577,515) or of gelatin (U.S. Pat. Nos. 2,800,457; 2,800,458), or they may consist of pheromone englobating multi-layer polymeric systems (A.C.S. 33-1976, pg. 283) or of hollow fiber systems consisting of capillaries with an open end through which the pheromone volatilizes (U.S. Pat. No. 4,017,030).

Such systems require a special elaboration both as far as concerns preparation thereof and, above all, for the successive distribution in the field.

A further drawback of some of those systems consists in supplying a release kinetics of the pheromone that is not linear, just due to the construction of the capsule itself.

The rate at which the pheromone is released is not only affected by the quantity of the pheromone, by the chemical composition of the capsules and by the chemical composition of the other formulation components, but also by environmental factors such as temperature, light and moisture.

A desired requisite for a formulation that will release a sufficient quantity of pheromone to permeate the air and achieve the effect of inhibiting the mating, is a controlled total and constant release for an adequate period of time.

THE PRESENT INVENTION

It is an object of this invention to provide a solid formulation with a controlled, total and constant release of the sex pheromone that will ensure hindering, as much as possible, the mating of the insects.

It has been observed that the formulations containing the active principle supported by an inert carrier will give place to a linear and total but fast release of the pheromone (see Example 2, infra-composition 11).

We have now found that formulations containing the active principle (pheromone) supported on inert carriers coated with film-forming resins will give rise to a controlled, total and, with an excellent approximation, linear pheromone release.

The aforementioned object, and other objects, are achieved by this invention in accordance with which solid formulations are provided consisting of an active substance which is a sex pheromone of insects and supported on an inert carrier coated with film-forming resin, a wetting agent, a dispersant and a sticker, an ultraviolet (U.V.) stabilizer and an antioxidant, and having the following composition:

|  | % by weight |
|---|---|
| A - active substance (sex pheromone) | 0.5–10 |
| B - film-forming resin | 5–30 |
| C - dispersant, wetting agent, sticker | 5–15 |
| D - U.V. stabilizer | 0.5–10 |
| E - antioxidant | 0.5–10 |
| F - inert carrier | to make 100% (25–88.5%) |

These formulations allow a controlled, total and sufficiently linear release of the active substance.

The release rate of the active substance is a function of both the chemical class of the chosen resin (given that for the different polymers the migration speed of the active substance is different in each instance) as well as of the quantity of deposited resin.

More particularly, the film-forming resins used according to this invention consist of carboxylated polyvinyl alcohol-based compounds, of compounds based on terpene polymers or of mixtures of chlorinated derivatives of natural rubber.

It is essential for the formulations of this invention to comprise a suitable U.V. stabilizer and a suitable antioxidant for protecting the chemical integrity of the active substance, both to guarantee the stability of the pheromone in the formulate and to preserve the pheromone itself for the longest possible time when the treatment is carried out in the field.

The selected U.V. stabilizers belong to the class of the benzophenone derivatives having a high molecular weight, in particular 2-hydroxy-4-octyloxy-benzophenone of the formula:

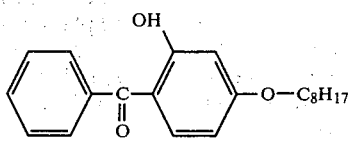

The selected antioxidants belong to the class of the derivatives of 2,6-di-terbutylphenol, more particularly stearyl 2,6-di-terbutylphenol propionate and pentaerythrite 2,6-di-terbutylphenol propionate.

Examples of wetting agents, dispersants and stickers used in the formulations are compounds based on mixtures of methacrylic polymer, nonylphenol, polyoxyethylates and sodium lignosulphonate.

The present formulations are prepared by known methods and following the known principles of the art.

Said formulations can be applied as wettable powders, according to standard application methods.

The sexual pheromones that constitute the active substance of the formulations according to this invention may be pheromones of different insects such as e.g.:

(E)-11-tetradecenal, pheromone of *Choristoneura fumiferana;*

(E,E)-8,10-dodecadienol, pheromone of *Laspeyresia pomonella* L.

(Z)-8-dodecylacetate, pheromone of *Grapholitha molesta,* Busk.;

(Z)-9-dodecenyl acetate, pheromone of *Clysia ambiguella* Hb.;

(E,Z)-7,9-dodecadienyl acetate, pheromone of *Lobesia botrana* Den & Schiff;

(Z)-11-tetradecenyl acetate and (E)-11-tetradecenyl acetate, pheromone of *Archips podanus* Scop.;

(Z-E)-9,11-tetradecadienyl acetate, pheromone of *Spodoptera littoralis* Boisd.;

(Z)-11-hexadecen-1-al, pheromone of *Heliothis armigera* HB.;

(Z,E)-7,11-hexadecadienylacetate and (Z,Z)-7,11 hexadecadienylacetate, pheromone of *Pectinophora gossypiella,* and other similar sexual pheromones.

The main inert materials on which the active principle is supported, are, for instance: calcined fossil meal, kaolin, micronized attapulgites, talc. The fossil meal has a composition based on Al, Fe, Ca, Mg, Na, K silicates; typical examples are: "Celite SCC", and "Celite 209". The kaolin has a composition mainly based on aluminum silicate; typical example: "Argirek B22". The useful attapulgites have compositions based on Al, Mg, Ca, Fe, Na, K silicates; typical example: "Diluex".

These formulations with controlled release have, among other advantages, the possibility of being applied by the methods and with the equipment usual for wettable powders, with quite appreciable economical advantages, and of being easily handled by any user.

The chemical compounds which are components of insect sex pheromones can be prepared according to known procedures. They have been described in various publications, examples of which are hereinbelow reported:

M. Beroza et al., Science 183, 89 (1974) [pheromone of *Laspeyresia pomonella*]

W. L. Roelofs et al., Nature 224, 723 (1969) [pheromone of *Grapholitha molesta*]

P. E. Sonnet, J. Org. Chem. 39, 3793 (1974) [pheromone of *Pectinophora gossipiella*]

B. F. Nesbitt et al., Nature Nev. Biol. 244, 208 (1973) [pheromone of *Spodoptera littoralis*]

J. C. Person et al., J. Insect Physiol. 20, 1181 (1974) [pheromone of *Archips podanus*]

H. Arn et al., Z. Naturforsch. 31C, 499 (1976) [pheromone of *Clysia ambiguella*]

H. Arn et al., Z. Naturforsch. 30, 722 (1975) [pheromone of *Lobesia botrana*]

C. J. Sanders et al., Can. Entomol 108, 1285 (1976) [pheromone of *Choristoneura fumiferana*]

Ohta Kyuji et al., Agric. Biol. Chem. 40(9), 1897 (1976) [pheromone of *Heliothis armigera*]

As herein before reported the inert materials are, for example, calcined fossil meal, kaolin, micronized attapulgite and talc. The commercially available products can suitably be used in the formulations object of the invention.

Characteristics of the fossil meal are: a bulk density comprised between 120 and 150 g/l, specific surface comprised between 4–6 $m^2/g$, pH of 10% aqueous suspension comprised between 6 and 8.

"Celite SSC" used in the examples is a fossil meals with characteristics according to those above reported.

The material named kaolin has the following characteristics: bulk density 320–460 g/l, specific surface 3–5 $m^2/g$, pH of 10% aqueous suspension 4–8.

Attapulgite is an inert material having the following characteristics: bulk density 150–300 g/l, specific surface 150–300 $m^2/g$. Other inert materials are colloidal silica (bulk density 100–180 g/l, specific surface 150–200 $m^2/g$) and talc consisting essentially of a mixture of silicates (bulk density 450–800 g/l, specific surface 2–4 $m^2/g$).

A high degree of purity in the inert materials does not represent an essential feature for the scope of the invention and the commercially available products can be conveniently used.

The formulations object of the invention contain also antioxidant products chosen amongst the derivatives of 2,6-di-terbutylphenol having antioxidant properties. Particularly useful are 2,6-di-terbutylphenol propionate of stearyl and of pentaerythritol[tetrakis-hydroxymethyl-metane C(CH2OH)4].

2,6-di-terbutylphenol propionate of stearyl is a name often used to indicate the ester of 3-(3,5-di-tert.butyl-4-hydroxy-phenyl)-propionic acid with stearic alcohol and having the formula:

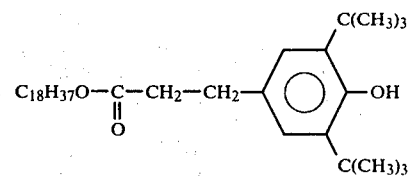

Similarly, 2,6-di-ter.butylphenol propionate of pentaerithritol indicates the tetrakis ester of 3-(3,5-di-tert.butyl-4-hydroxy-phenyl)-propionic acid with pentaerithritol [C(CH₂OH)₄], having the formula:

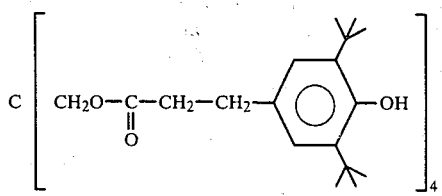

Further additives to be used in the formulations object of the invention are wetting agents, dispersants, and stickers. Suitable wetting agents are polyoxyethylated alkyl phenols, for example—polyoxyethylated nonylphenol and particularly polyoxyethylated nonylphenol containing 40-80 moles of ethylene oxide per mole of nonylphenol.

As a sticker, sodium polymethacrylate with molecular weight comprised between 10,000 and 40,000, can be used.

"Polymer PS 50" used in the examples is a commercially available mixture of polymethacrylate and polyoxyethylated nonylphenol in the ratio 9:1.

Examples of dispersants which can be used in the formulations object of the invention are sodium lignosulphonates having a degree of sulphonation comprised between 0.5 and 5. "Reax 45 A" used in the examples is a commercially available sodium lignosulphonate whose characteristics are comprised in the hereabove reported range.

The wetting agent, sticker and dispersant can be used in the formulations object of the invention as a mixture consisting of 1-10% by weight of wetting agent, 50-94% by weight of sticker and 5-40% by weight of dispersant, the total being 100%.

An amount of such mixture comprised between 5 and 15% by weight is used in the formulations.

The use of said additives is related to the fact that the formulations object of the invention are in the form of wettable powder. The specific compounds hereabove mentioned have been found to be particularly suited for the described formulations, without being a critical feature.

The film forming resins, consist of terpene polymers, chlorinated derivatives of natural rubber and carboxylated polyvinylalcohol.

Terpene polymers consist essentially of polymerized pinene, having a softening range comprised between 10° and 135° C. and a molecular weight comprised between 100–1300. "Picolite S85" is an example of such polymers.

The chlorinated derivatives on natural rubber consist of chlorinated natural rubber having a content in chlorine of about 65–68% by weight and whose monomeric units are $(C_5H_7Cl_3)$ and $(C_5H_6Cl_4)$, the viscosity of a 20% solution in toluene ranges between 5 and 180 cps (Hottler method). "Chlortex 70" used in the examples is chlorinated natural rubber whose characteristics are in the range hereabove reported.

Carboxylated polyvinyl alcohol is a copolymer of vinylacetate and unsaturated carboxylic acids having a carboxylation degree of 4–6 g/100 g polymer, a molecular weight comprised between 500 and 1500 and a softening range of 80°–130° C. "Vinavyl 4" used in the examples is a carboxylated polyvinylalcohol whose characteristics are in accordance with those above reported.

The following examples are given to illustrate the invention in more detail, and are not intended to be limiting.

EXAMPLE 1

This example illustrates the tests performed for establishing the selectivity of the possible stabilizers.

100 g of the compositions from 1 to 10 reported in Table I were prepared by depositing, from a solution in $CH_2Cl_2$, the active substance (henceforth called a.s.) and the possible stabilizers on the pre-selected carrier, subsequently allowing the solvent to evaporate.

50 g of such compositions were maintained for 14 days at room temperature, and 50 grams of the compositions were kept at a thermostatically stabilized temperature of 40° C. At the end of this period, the residual a.s., after extraction with n-hexane, was evaluated by gas-liquid chromatography.

TABLE I

| COMPONENTS | COMPOSITIONS | | | | | | | | | |
|---|---|---|---|---|---|---|---|---|---|---|
| | 1 | 2 | 3 | 4 | 5 | 6 | 7 | 8 | 9 | 10 |
| (Z,E)-9,11 $C_{14}A_c$ (a.s.) (1) | 5 | 5 | 5 | 5 | 5 | 5 | 5 | 5 | 5 | 5 |
| Clortex 70 (2) | 95 | | | 15 | | | 15 | | | |
| VINAVIL C4 (3) | | 95 | | | 15 | | | | | |
| PICOLITE S85 (4) | | | 95 | | | 15 | | 15 | | |
| UV 531 (5) | | | | | | | 5 | 5 | | 5 |
| IRGANOX 1010 (6) | | | | | | | 5 | 5 | | 5 |
| CELITE SSC (7) | | | | 80 | 80 | 80 | 70 | 70 | 95 | 85 |
| Degradation % after 14 days at: | | | | | | | | | | |
| Room temp. | 9.1 | 12.3 | 6.2 | 24.8 | 31.4 | 7.3 | <0.1 | <0.1 | 83 | <0.1 |
| 40° C. | 23.6 | 33.5 | 18.4 | 28.2 | 35.2 | 10.1 | <0.1 | <0.1 | 82 | <0.1 |

Notes to Table I
(1) Pheromone of *Spodoptera littoralis* (Z,E)-9,11-tetradecadienyl acetate.
(2) "Clortex" - registered trademark of Caffaro- mixtures of chlorinated derivatives of natural rubber.
(3) "VINAVIL C4" - registered trademark of Montedison - carboxylated polyvinylalcohols.
(4) "PICOLITE S85" - registered trademark of Chem-Plast. - terpene polymers.
(5) U.V. 531 - 2-hydroxy-4-n.octyloxybenzophenone.
(6) "Irganox 1010" - pentaerythrite 2,6-di-terbutylphenolpropionate.
(7) "Celite SSC" - registered trademark of Johns-Manville - fossil meal.

The samples 7, 8 and 10 were subjected to a U.V. radiation test under the following conditions:

solar spectrum lamp with emission of U.V. radiation; distance of samples from the lamp—20 cm; temperature—40° C.

At different times, part of the sample is drawn and the residual active substance is evaluated, after extraction with n-hexane, by means of gas:liquid chromatography. The results are recorded in Table II.

TABLE II

| Sample No. | a.s.: residue % after time of exposure minutes | | |
|---|---|---|---|
| | 0 | 1440 | 2280 |
| 7 | 100 | 67.8 | 49.6 |
| 8 | 100 | 66.3 | 37.8 |
| 10 | 100 | 44.1 | 8.0 |

EXAMPLE 2

Release tests of (Z,E)-9,11 $C_{14}Ac$ stabilized with Celite SSC and with compositions based on Celite SSC with film-forming coating resin.

100 g of compositions 11, 12 and 13, shown in Table III, were prepared by depositing, from a solution in $CH_2Cl_2$, the a.s., the stabilizers and the film-forming resin onto the powdery carrier and by successively allowing the solvent to evaporate. The samples of Table III were then exposed, in a suitable cell, to the following conditions:

temperature—30° C.;
artificial lighting—15 hours on 24 hours;
air change—160 cu.mt./hour corresponding to 6 total changes of the air in the cell per hour.

At different times, drawings from the exposed samples were effected and, after extraction with n-hexane, the percentage of residual a.s. was calculated. The results are recorded in Table III below.

TABLE III

| Components | Compositions | | |
|---|---|---|---|
| | 11 | 12 | 13 |
| (Z,E)-9,11 $C_{14}Ac$ | 5 | 5 | 5 |
| U.V. 531 | 5 | 5 | 5 |
| IRGANOX 1010 | 5 | 5 | 5 |
| CLORTEX 70 | — | 10 | — |
| PICOLITE S 85 | — | — | 10 |
| CELITE SSC | 85 | 75 | 75 |

| Sample No. | Data of the release tests: a.s.: % of residue after time of exposure (hours) | | | | | | |
|---|---|---|---|---|---|---|---|
| | 0 | 30 | 118 | 169 | 300 | 430 | 500 |
| 11 | 100 | 93.7 | 75.8 | 67.0 | 41.2 | 16.8 | 0.0 |
| 12 | 100 | 98.1 | 93.1 | 94.0 | 81.5 | 73.77 | 70.0 |
| 13 | 100 | 97.7 | 88.6 | 85.3 | 75.0 | 68.5 | 57.3 |

EXAMPLE 3

Preparation of Complete Formulations

100 Grams of formulates 14, 15 and 16, shown in Table IV, were prepared by depositing, from a solution in $CH_2Cl_2$, the a.s., the stabilizers and the resin onto the powdery carrier.

The solvent was allowed to evaporate at room temperature. There were then admixed the indicated quantities of wetting agent, dispersant and sticker agent, and the mixture was homogenized by passing it through a suitable mechanical mixer.

TABLE IV

| Components | Formulations | | |
|---|---|---|---|
| | 14 | 15 | 16 |
| (Z,E)-9,11 $C_{14}Ac$ | 5 | 5 | 5 |
| IRGANOX 1010 | 5 | 5 | 5 |
| U.V. 531 | 5 | 5 | 5 |
| Clortex 70 | 15 | 30 | — |
| PICOLITE S 85 | — | — | 20 |
| REAX 45 A[1] | 5 | 5 | 5 |
| POLYMER PS50 (RP 10)[2] | 10 | 10 | 10 |
| CELITE SSC | 55 | 40 | 50 |
| Degradation percentage after 14 days: | | | |
| room temperature | <0.1 | <0.1 | <0.1 |
| at 40° C. | <0.1 | <0.1 | <0.1 |

Notes to Table IV:
[1]"Reax 45A" - registered trademark of Westvaco - sodium lignosulphonate.
[2]"Polymer PS 50 (RP 10)" - registered trademark of ROL-mixtures of methacrylic polymer and nonylphenol-polyoxyethylate.

EXAMPLE 4

Release Tests of Complete Formulates

With formulations 14, 15 and 16 there were carried out release tests under the same conditions and following the same procedures as in Example 2. The results thus obtained are recorded in the following table.

| Sample No. | DATA OF RELEASE TESTS a.s.: % of residue after exposure time (hours) | | | | | | |
|---|---|---|---|---|---|---|---|
| | 0 | 95 | 168 | 264 | 624 | 1104 | 1224 |
| 14 | 100 | 94.8 | 91.1 | 88.3 | 67.1 | 37.9 | 35.3 |
| 15 | 100 | | 94.3 | | 88.1 | 72.0 | |
| 16 | 100 | | 90.8 | | 79.4 | 59.5 | |

EXAMPLE 5

Confusion Method Test in Egypt

With formulation 14 of Example 4 there were conducted confusion tests on *Spodoptera littoralis* in Egypt, in the Faiyum region, locality Tamiya, for the periods June 8 to June 30, 1979 and July 1 to July 6, 1979.

The formulate was applied on an area of 2 Feddan (1 Feddan=4,200 sq.mt.) cultivated with cotton, with a dose of 4 g of a.s./Feddan.

An 0.2% aqueous suspension of the formulate was applied from the ground by means of a standard sprinkling device.

The effectiveness of the confusion was assessed by comparing the number of adult males captured in 4 traps baited with the same pheromone and placed one pair inside the treated zone and the other pair in the untreated zone (witness) adjacent to the treated zone. The data are recorded in Table V.

TABLE V

| | June 8, 1979 | 9 | 10 | 11 | 12 | 13 | 14[1] | 15 | 16 | 17 | 18 | 19 | 20 | 21 |
|---|---|---|---|---|---|---|---|---|---|---|---|---|---|---|
| TREATED | | | | | | | | | | | | | | |

TABLE V-continued

| ZONE | | | | | | | | | | | | | | |
|---|---|---|---|---|---|---|---|---|---|---|---|---|---|---|
| Trap 1 | 56 | 103 | 207 | 137 | 268 | 254 | 285 | 0 | 9 | 26 | 84 | 6 | 12 | 14 |
| Trap 2 | 36 | 69 | 19 | 93 | 159 | 168 | 382 | 15 | 139 | 98 | 127 | 105 | 55 | 42 |
| Total captures | 92 | 172 | 398 | 230 | 427 | 422 | 667 | 15 | 148 | 124 | 221 | 111 | 67 | 56 |
| Trap 3 | 51 | 33 | 112 | 89 | 162 | 195 | 448 | 67 | 213 | 195 | 325 | 25 | 4 | 13 |
| Trap 4 | 59 | 77 | 216 | 229 | 256 | 147 | 395 | 36 | 394 | 281 | 257 | 246 | 131 | 186 |
| Total captures | 110 | 100 | 328 | 318 | 418 | 342 | 843 | 103 | 610 | 476 | 582 | 271 | 135 | 199 |
| T°C max. | 35 | 33 | 35 | 37 | 40 | 42 | 40 | 39 | 39 | 40 | 41 | 43 | 43 | 43 |
| min. | 21 | 23 | 21 | 22 | 22 | 22 | 23 | 23 | 23 | 22 | 23 | 24 | 25 | 24 |
| Relative humidity % | 49 | 59 | 42 | 44 | 32 | 36 | 34 | 35 | 38 | 35 | 48 | 42 | 42 | 40 |

| | 22 | 23 | 24 | 25 | 26 | 27 | 28 | 29 | 30 | July 1, 1979 | 2 | 3 | 4 | 5 | 6 |
|---|---|---|---|---|---|---|---|---|---|---|---|---|---|---|---|
| TREATED ZONE | | | | | | | | | | | | | | | |
| Trap 1 | 6 | 3 | 5 | 21 | 10 | 1 | 3 | 3 | 2 | 0 | 0 | 3 | 0 | 0 | 0 |
| Trap 2 | 0 | 0 | 6 | 28 | 6 | 4 | 7 | 0 | 0 | 0 | 0 | 1 | 0 | 0 | 0 |
| Total captures | 6 | 3 | 11 | 49 | 16 | 5 | 10 | 3 | 2 | 0 | 0 | 4 | 0 | 0 | 0 |
| WITNESS | | | | | | | | | | | | | | | |
| Trap 3 | 13 | 12 | 26 | 2 | 11 | 5 | 7 | 0 | 3 | 0 | 0 | 2 | 1 | 3 | 2 |
| Trap 4 | 98 | 62 | 45 | 264 | 145 | 38 | 27 | 5 | 12 | 4 | 5 | 7 | 12 | 15 | 16 |
| Total captures | 111 | 74 | 71 | 266 | 156 | 43 | 34 | 5 | 15 | 4 | 5 | 9 | 13 | 18 | 18 |
| Temp. °C.: max. | 42 | 41 | 45 | 45 | 45 | 43 | 43 | 40 | 40 | 39 | 41 | 38 | 41 | 41 | 42 |
| min. | 23 | 24 | 26 | 24 | 23 | 22 | 22 | 21 | 22 | 21 | 20 | 21 | 22 | 21 | 21 |
| Relative humidity % | 46 | 42 | 42 | 52 | 52 | 49 | 48 | 50 | 42 | 42 | 50 | 50 | 44 | 44 | 46 |

[1] day of the starting of the treatment carried out during evening hours

EXAMPLE 6

The formulations shown in Table VI were prepared following the procedures of Example 3.

TABLE VI

| COMPONENTS | 17 | 18 |
|---|---|---|
| (E,E)-8,10 $C_{12}$, OH[1] | 5 | 5 |
| UV 531 | 5 | 5 |
| Irganox 1010 | 5 | 5 |
| Celite SSC | 60 | 60 |
| Clortex 70 | 10 | — |
| Picolite S85 | — | 10 |
| PS 50 (RP 10) polymer | 10 | 10 |
| Reax 45 A | 5 | 5 |

Note to Table VI
[1] Pheromone of *Laspeyresia pomonella*

Release tests were carried out with samples of formulations 17 and 18, under the same conditions and by the same procedures described in Example 2. The results are shown in Table VII.

TABLE VII

| Sample No. | d.s.: residual % after exposure time (hours) | | | | | | |
|---|---|---|---|---|---|---|---|
| | 0 | 30 | 96 | 230 | 400 | 660 | 1260 |
| 17 | 100 | 99.5 | 91.7 | 92.8 | 82.6 | 71.7 | 47.4 |
| 18 | 100 | 96.4 | 93.1 | 92.2 | 88.4 | 77.5 | 56.0 |

EXAMPLE 7

Following the same procedures as those indicated in Example 3, there were prepared formulations 19 and 20 in Table VIII.

TABLE VIII

| COMPONENTS | 19 | 20 |
|---|---|---|
| (Z) 11 hexadecen-1-al[1] | 5 | — |
| (E) 11 tetradecen-1-al[2] | — | 5 |

TABLE VIII-continued

| COMPONENTS | 19 | 20 |
|---|---|---|
| UV 531 | 5 | 5 |
| Irganox 1010 | 5 | 5 |
| Celite SSC | 55 | 55 |
| Clortex 70 | 15 | 15 |
| PS 50 (RP 10) polymer | 10 | 10 |
| Reax 45 A | 5 | 5 |

Notes to Table VIII:
[1] Pheromone of *Heliothis armigera*;
[2] Pheromone of *Choristoneura fumiferana*.

Following the procedures of Example 2, release tests were carried out with formulation No. 19. The results thereby obtained have been recorded in following Table IX.

TABLE IX

| Sample No. | a.s.: residual % after exposure time (hours) | | | | | |
|---|---|---|---|---|---|---|
| | 0 | 75 | 195 | 410 | 570 | 875 |
| 19 | 100 | 93.7 | 92.1 | 67.9 | 64.7 | 46.6 |

We claim:
1. A solid formulation consisting of: a sex insect pheromone as an active substance, supported on an inert material coated with a film-forming resin, a wetting agent, a dispersant and a sticker, an ultraviolet stabilizer, and an antioxidant, and having the following composition, the quantities being in percent by weight:

| | | |
|---|---|---|
| A | Active substance - sex pheromone | 0.5-10 |
| B | Film-forming resin selected amongst terpene polymers, chlorinated natural rubber or carboxylated polyvinylalcohol | 5-30 |
| C | Mixture of a polyoxyethylated alkyl phenol (1-10% b.w.), sodium polymethacrylate (50-94% b.w.) and sodium lignosulphonate (5-40% b.w.), the total being 100% | 5-15 |

-continued

| | | |
|---|---|---|
| D | U.V. Stabilizer consisting of derivatives of benzophenone having stabilizing properties | 0.5–10 |
| E | Antioxidant selected amongst the esters of 3-(3,5-di-tert.butyl-4-hydroxy-phenyl)-propionic acid with stearic alcohol or with pentaerithritol (tetrakis ester) | 0.5–10 |
| F | Inert carrier consisting essentially of a material selected amongst fossil meal, kaolin, attapulgite and talc | to 100%. |

2. A formulation according to claim 1, in which the active substance is used in an amount of about 5% by weight.

3. A formulation according to claim 1, in which the active substance is (Z,E)-9,11-tetradecadienyl acetate, pheromone of *Spodoptera littoralis*.

4. A formulation according to claim 1, in which the active substance is (E,E)-8,10-dodecadienol, pheromone of *Laspeyresia pomonella*.

5. A formulation according to claim 1, in which the active substance is (Z)-11-hexadecenal, pheromone of *Heliothis armigera*.

6. A formulation according to claim 1, in which the active substance is (E)-11-tetradecenal, pheromone of *Choristoneura fumifera*.

7. A formulation according to claim 1, in which the film-forming resin is used in an amount of about 15 to about 25% by weight.

8. A formulation according to claim 1, in which the ultra-violet stabilizer is 2-hydroxy-4-octyloxy-benzophenone.

9. A formulation according to claim 1, in which the polyoxyethylated alkyphenol is polyoxyethylated nonylphenol with a content of ethylene oxide corresponding to 40–80 moles per mole of nonylphenol.

10. A formulation according to claim 1, in which the sodium polymethacrylate has a molecular weight comprised between 10,000 and 40,000.

11. A formulation according to claim 1, in which the sodium lignosulphonate has a degree of sulphonation comprised between 0.5 and 5.

12. A formulation according to claim 1, consisting of

| | | |
|---|---|---|
| A - | Sex pheromone | 5% by weight |
| B - | Film-forming resin | 15% by weight |
| C - | Mixture of nonylphenol polyoxyethylated, sodium polymethacrylate and sodium ligno sulphonate in the weight ratio 1:9:5 | 15% by weight |
| D - | 2-hydroxy-4-octyloxy-benzophenone | 5% by weight |
| E - | Ester of 3-(3,5-di-tert.butyl-4-hydroxy-phenyl)-propionic acid with stearic alcohol or with pentaerithritol (tetrakis ester) | 5% by weight |
| F - | Inert carrier | 55% by weight. |

13. A formulation according to claim 1, consisting of

| | | |
|---|---|---|
| A - | Sex pheromone | 5% by weight |
| B - | Film-forming resin | 20% by weight |
| C - | Mixture of nonylphenol polyoxyethylated, sodium polymethacrylate and sodium ligno sulphonate in the weight ratio 1:9:5 | 15% by weight |
| D - | 2-hydroxy-4-octyloxy-benzophenone | 5% by weight |
| E - | Ester of 3-(3,5-di-tert.butyl-4-hydroxy-phenyl)-propionic acid with stearic alcohol or with pentaerithritol (tetrakis ester) | 5% by weight |
| F - | Inert carrier | 50% by weight |

14. A formulation according to claim 1, consisting of

| | | |
|---|---|---|
| A - | Sex pheromone | 5% by weight |
| B - | Film-forming resin | 10% by weight |
| C - | Mixture of nonylphenol polyoxyethylated, sodium polymethacrylate and sodium ligno sulphonate in the weight ratio 1:9:5 | 15% by weight |
| D - | 2-hydroxy-4-octyloxy-benzophenone | 5% by weight |
| E - | Ester of 3-(3,5-di-tert.butyl-4-hydroxy-phenyl)-propionic acid with stearic alcohol or with pentaerithritol (tetrakis ester) | 5% by weight |
| F - | Inert carrier | 60% by weight. |

15. A formulation according to claim 1, consisting of

| | | |
|---|---|---|
| A - | Sex pheromone | 5% by weight |
| B - | Film-forming resin | 30% by weight |
| C - | Mixture of nonylphenol polyoxyethylated, sodium polymethacrylate and sodium ligno sulphonate in the weight ratio 1:9:5 | 15% by weight |
| D - | 2-hydroxy-4-octyloxy-benzophenone | 5% by weight |
| E - | Ester of 3-(3,5-di-tert.butyl-4-hydroxy-phenyl)-propionic acid with stearic alcohol or with pentaerithritol (tetrakis ester) | 5% by weight |
| F - | Inert carrier | 40% by weight. |

16. A method for controlling harmful species of insects by distributing in the infested area the insect sex pheromone so as to prevent copulation, characterized in that an effective amount of a formulation according to claim 1 is distributed in the infested area.

* * * * *